US012280074B2

United States Patent
Devos et al.

(10) Patent No.: US 12,280,074 B2
(45) Date of Patent: *Apr. 22, 2025

(54) PREPARATION OF PLATELET PELLET LYSATE AND ITS USE FOR TREATING NEUROLOGICAL DISORDERS

(71) Applicants: CENTRE HOSPITALIER REGIONAL ET UNIVERSITAIRE DE LILLE (CHRU), Lille (FR); UNIVERSITE DE LILLE, Lille (FR); UNIVERSITE DU LITTORAL COTE D'OPALE, Dunkirk (FR); INSERM (INSTITUT NATIONAL DE LA SANTE ET DE LA RECHERCHE MEDICALE), Paris (FR); TAIPEI MEDICAL UNIVERSITY, Taipei (TW)

(72) Inventors: David Devos, Lille (FR); Thierry Burnouf, Lille (FR); Jean-christophe Devedjian, Lille (FR); Ming-Li Chou, Taoyuan (TW)

(73) Assignees: Centre Hospitalier Regional et Universitaire de Lille (CHRU), Lille (FR); Universite de Lille, Lille (FR); Universite du Littoral Cote D'Opale, Dunkirk (FR); Inserm (Institut National de La Sante et de la Recherche Medicale), Paris (FR); Taipei Medical University, Taipei (TW)

( * ) Notice: Subject to any disclaimer, the term of this patent is extended or adjusted under 35 U.S.C. 154(b) by 578 days.

This patent is subject to a terminal disclaimer.

(21) Appl. No.: 16/087,471

(22) PCT Filed: Mar. 23, 2017

(86) PCT No.: PCT/EP2017/057004
§ 371 (c)(1),
(2) Date: Sep. 21, 2018

(87) PCT Pub. No.: WO2017/162830
PCT Pub. Date: Sep. 28, 2017

(65) Prior Publication Data
US 2019/0099448 A1 Apr. 4, 2019

(30) Foreign Application Priority Data

Mar. 23, 2016 (EP) ..................... 16305332

(51) Int. Cl.
*A61K 35/19* (2015.01)
*A61P 25/00* (2006.01)
*A61P 25/16* (2006.01)
*A61P 25/28* (2006.01)

(52) U.S. Cl.
CPC .............. *A61K 35/19* (2013.01); *A61P 25/16* (2018.01); *A61P 25/28* (2018.01)

(58) Field of Classification Search
CPC ................................ A61K 35/19; A61P 25/00
See application file for complete search history.

(56) References Cited

U.S. PATENT DOCUMENTS

| 11,744,863 B2 * | 9/2023 | Devos et al. | .......... A61K 35/19 |
| 2007/0265203 A1 * | 11/2007 | Eriksson et al. | ....... A61K 38/00 |
| | | | 514/12 |

FOREIGN PATENT DOCUMENTS

WO    WO2009155069 A1 *  12/2009  ............. A01N 43/04

OTHER PUBLICATIONS

Choi et al. "Effect of platelet lysate on growth and sulfated glycosaminoglycan synthesis in articular chondrocyte cultures", Arthritis & Rheumatism, vol. 23, No. 2, 1980, pp. 220-224, (Year: 1980).*
Hayon et al. "Platelet lysates stimulate angiogenesis, neurogenesis and neuroprotection after stroke" Thromb Haemost 2013, 110: 323-330. (Year: 2013).*
Chou et al. "Ex vivo Expansion of Bovine Corneal Endothelial Cells in Xeno-Free Medium Supplemented with Platelet Releasate" PLOS ONE 2014, 9(6): e99145, 8 pages. (Year: 2014).*
Anitua et al. "Intranasal Delivery of Plasma and Platelet Growth Factors Using PRGF-Endoret System Enhances Neurogenesis in a Mouse Model of Alzheimer's Disease" PLoS ONE 2013, 8(9): e73118, 13 pages. (Year: 2013).*
Bonin et al. "Treatment of refractory acute GVHD with third-party MSC expanded in platelet lysate-containing medium" Bone Marrow Transplantation (2009) 43, 245-251. (Year: 2009).*
Choi et al. (1980) "Effect of platelet lysate on growth and sulfated glycosaminoglycan synthesis in articular chondrocyte cultures" Arthritis and Rheumatism, vol. 22, No. 2, pp. 220-224. (Year: 1980).*
Copland et al. (2013) "The effect of platelet lysate fibrinogen on the functionality of MSCs in immunotherapy" Biomaterials, 34(32), 7840-7850. (Year: 2013).*

(Continued)

*Primary Examiner* — Teresa E Knight
*Assistant Examiner* — James Joseph Graber

(57) ABSTRACT

A process for preparing a modified heat-treated platelet pellet lysate, said process comprising the steps of: a) Providing a platelet pellet lysate, b) Heat-treating the platelet pellet lysate at a temperature of 55° C. to 65° C. during 20 to 40 minutes, c) Purifying the heat-treated platelet pellet lysate of step b) so as to obtain a modified heat treated platelet pellet lysate having a total protein content of less than 70% of the total protein content of the platelet pellet lysate of step a).

25 Claims, 12 Drawing Sheets

(56) References Cited

OTHER PUBLICATIONS

Figure 1:
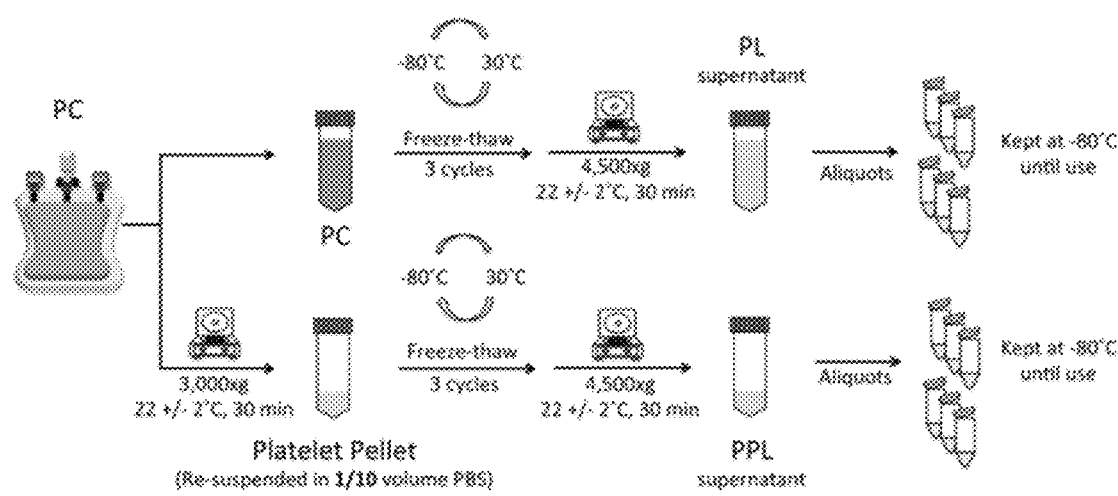

Chou et al. (2017) "Tailor-made purified human platelet lysate concentrated in neurotrophins for treatment of Parkinson's disease" Biomaterials, 142, 77-89. (Year: 2017).*
The International Search Report and Written Opinion, mailed on May 9, 2017, in the related PCT Appl. No. PCT/EP2017/057004.
Choi et al: "Effect of platelet lysate on growth and sulfated glycosaminoglycan synthesis in articular chondrocyte cultures", Arthritis & Rheumatism, vol. 23, No. 2, Jan. 1, 1980 (Jan. 1, 1980), pp. 220-224.
Tang et al.: "Survival effect ofPDGF-CC rescues neurons from apoptosis in both brain and retina by regulating GSK3 beta phosphorylation", Journal of Experimental Medicine, vol. 207, 2010, pp. 867-880.
Hara et al. "Platelets as a Source of Growth-promoting Factor(s) for Tumor Cells", Cancer Research, Apr. 1, 1980 (Apr. 1, 1980), pp. 1212-1216.
Aron et al., "Repairing the parkinsonian brain with neurotrophic factors," Trends Neurosci 2011;34: 88-100.
Barrientos et al., "Growth factors and cytokines in wound healing," Wound Repair Regen 2008;16: 585-601.
Blair et al., "Platelet alpha-granules: basic biology and clinical correlates," Blood Rev 2009;23: 177-89.
Burnouf et al., "Nanofiltration of plasma bio-pharmaceutical products [invited review] . Haemophilia," 2003, 9: 24-37.
Burnouf et al., Place of nanofiltration for assuring viral safety of biologicals. Current Nanoscience, 2005; 1: 189-201.
Burnouf et al., "Human platelet concentrates: a source of solvent/detergent-treated highly enriched brain-derived neurotrophic factor," Transfusion 2012;52: 1721-8.
Burnouf et al., "A chromatographically purified human TGF-betaI fraction from virally inactivated platelet lysates," Vox Sang 2011;101: 215-20.
Burnouf et al., "Antimicrobial activity of platelet (PLT)-poor plasma, PLT-rich plasma, PLT gel, and solvent/detergent-treated PLT lysate biomaterials against wound bacteria," Transfusion 2013 ;53: 138-46.
Burnouf et al., "Blood-derived biomaterials and, platelet growth factors in regenerative medicine," Blood Rev 2013;27: 77-89.
Falk et al., "Vascular endothelial growth factor-B is neuroprotective in an in vivo rat model of Parkinson's disease," Neurosci Lett 2011;496: 43-7.
Gash et al., "Functional recovery in parkinsonian monkeys treated with GDNF," Nature 1996;380: 252-5.
Gonzalez et al., "Antiparkinsonian trophic action of glial cell line-derived neurotrophic factor and transforming growth factor beta 1 is enhanced after co-infusion in rats," Experimental Neurology 2010;226: 136-47.
Hayon et al., "Platelet lysates stimulate angiogenesis, neurogenesis and neuroprotection after stroke," Thromb Haemost 2013;110: 323-30.
Hefti et al., "Function of neurotrophic factors in the adult and aging brain and their possible use in the treatment of neurodegenerative diseases," Neurobiol Aging 1989;10:515-33.
Hoffer et al., "Glial cell line-derived neurotrophic factor reverses toxin-induced injury to midbrain dopaminergic neurons in vivo," Neurosci Lett 1994;182: 107-11.
Huang et al., "Neurotrophins: roles in neuronal development and function," Annu Rev Neurosci 2001;24: 677-736.
Kearns et al., "GDNF protects nigral dopamine neurons against 6-hydroxydopamine in vivo," Brain Res 1995;672: 104-11.
Kirik et al., "Localized striatal delivery of GDNF as a treatment for Parkinson disease," Nat Neurosci 2004;7: 105-10.
Klein HG, "Should blood be an essential medicine?" N Engl J Med 2013;368: 199-201.
Laloux et al., "MPTP-treated mice: long-lasting loss of nigral TH-ir neurons but not paradoxical sleep alterations," Experimental Brain Research 2008;186: 635-42.
Mohapel et al., "Platelet-derived growth factor (PDGF-BB) and brain-derived neurotrophic factor (BDNF) induce striatal neurogenesis in adult rats with 6-hydroxydopamine lesions," Neuroscience 2005;132: 767-76.
Nurden et al., "Platelets and wound healing," Front Biosci 2008;13: 3532-48.
Nutt et al., "Randomized, double-blind trial of glial cell line-derived neurotrophic factor (GDNF) in PD," Neurology 2003;60: 69-73.
Rodrigues et al., "Challenges and Promises in the Development of Neurotrophic Factor-Based Therapies for Parkinson's Disease," Drugs & Aging 2014;31: 239-61.
Roussa et al, "TGF-beta in dopamine neuron development, maintenance and neuroprotection," Adv Exp Med Biol 2009;651: 81-90.
Ruozi et al., "Neurotrophic factors and neurodegenerative diseases: a delivery issue," Int. Rev. Neurobiol 2012;102: 207-47.
Ryu et al., "Fibrinogen signal transduction in the nervous system. Journal of thrombosis and heamostasis," 2009; vol. 7, issue supplement si, 151-154.
Santo et al., "Chitosan-chondrotin sulphate nanoparticles for controlled delivery of platelet lysates in bone regenerative medicine. Journal of Tissue Engineering and Regenerative Medicine," Dec. 2012, vol. 6, issue S3, pp. s47-s59.
Schabitz et al., "Intravenous brain-derived neurotrophic factor enhances poststroke sensorimotor recovery and stimulates neurogenesis," Stroke 2007;38:2165-72.
Scholz et al., "Rapid, complete and large-scale generation of post-mitotic neurons from the human LUHMES cell line," J Neurochem 2011;119: 957-71.
Su et al., "Quantitative assessment of the kinetics of growth factors release from platelet gel," Transfusion 2008;48: 2414-20.
Su CY, Kuo YP, Lin YC, et al. A virally inactivated functional growth factor preparation from human platelet concentrates. Vox Sang 2009;97: 119-28.
Timmer et al., "Fibroblast growth factor (FGF)-2 and FGF receptor 3 are required for the development of the substantia nigra, and FGF-2 plays a crucial role for the rescue of dopaminergic neurons after 6-hydroxydopamine lesion," J Neurosci 2007;27: 459-71.
Tomac et al., "Protection and repair of the nigrostriatal dopaminergic system by GDNF in vivo," Nature 1995;373: 335-9.
Burnouf et al., "Human platelet lysate: replacing fetal bovine serum as a gold standard for human cell propagation?" Biomaterials;76: 371-87, Jan. 2016.
Golebiewska et al., "Platelet secretion: From haemostasis to wound healing and beyond," Blood Rev;29: 153-62, May 2015.
Shih et al., "Preparation, quality criteria, and properties of human blood platelet lysate supplements for ex vivo stem cell expansion," New Biotechnology, vol. 32, Issue 1, pp. 199-211, Jan. 25, 2015.

* cited by examiner

| Protein | compared to 37°C | | 56°C/37°C | | 65°C/37°C | |
|---|---|---|---|---|---|---|
| | 56°C | 65°C | Average | SD | Average | SD |
| Adiponectin | ↑ | ↑ | 1.492 | 0.026 | 1.723 | 0.128 |
| Aggrecan | --- | --- | 0.962 | 0.030 | 1.022 | 0.022 |
| Angiogenin | --- | ↓ | 1.107 | 0.013 | 0.144 | 0.005 |
| Angiopoietin-1 | ↓ | ↓ | 0.474 | 0.001 | 0.791 | 0.026 |
| Angiopoietin-2 | --- | --- | 0.847 | 0.028 | 0.903 | 0.001 |
| BAFF | --- | --- | 0.920 | 0.033 | 1.061 | 0.017 |
| BDNF | ↓ | ↓ | 0.442 | 0.036 | 0.753 | 0.028 |
| Complement Component C5/C5a | --- | --- | 0.923 | 0.013 | 1.015 | 0.003 |
| CD14 | --- | ↓ | 0.881 | 0.013 | 0.697 | 0.002 |
| CD30 | --- | --- | 0.906 | 0.007 | 0.991 | 0.025 |
| Complement Factor D | ↓ | ↓ | 0.394 | 0.001 | 0.186 | 0.006 |
| C-Reactive Protein | ↑ | ↓ | 1.531 | 0.010 | 0.676 | 0.020 |
| Cystatin C | ↑ | --- | 1.255 | 0.012 | 1.010 | 0.021 |
| Dkk-1 | --- | ↓ | 0.785 | 0.007 | 0.799 | 0.010 |
| DPPIV | --- | --- | 1.047 | 0.008 | 0.848 | 0.015 |
| EGF | --- | ↓ | 0.892 | 0.010 | 0.590 | 0.015 |
| EMMPRIN | --- | --- | 1.094 | 0.001 | 0.859 | 0.001 |
| ENA-78 | ↓ | ↓ | 0.415 | 0.007 | 0.383 | 0.006 |
| Endoglin | ↓ | ↓ | 0.738 | 0.035 | 0.782 | 0.006 |
| FGF basic | --- | --- | 0.973 | 0.056 | 0.820 | 0.027 |
| FGF-19 | --- | --- | 0.899 | 0.016 | 0.979 | 0.022 |
| IGFBP-2 | ↓ | --- | 0.790 | 0.005 | 0.974 | 0.003 |
| IL-1α | --- | --- | 0.855 | 0.027 | 0.871 | 0.009 |
| IL-17A | --- | --- | 0.989 | 0.040 | 1.021 | 0.008 |
| IP-10 | --- | --- | 0.955 | 0.015 | 0.919 | 0.022 |
| Lipocalin-2 | ↑ | ↑ | 1.446 | 0.251 | 1.565 | 0.220 |
| MIF | --- | --- | 1.114 | 0.007 | 0.833 | 0.000 |
| Osteopontin | --- | --- | 0.978 | 0.246 | 1.192 | 0.027 |
| PDGF-AA | --- | ↑ | 1.105 | 0.032 | 1.621 | 0.019 |
| PDGF-AB/BB | --- | ↑ | 0.938 | 0.059 | 1.785 | 0.014 |
| Pentraxin-3 | --- | --- | 0.876 | 0.031 | 1.007 | 0.081 |
| PF4 | --- | --- | 0.911 | 0.002 | 1.106 | 0.028 |
| RANTES | --- | ↓ | 0.888 | 0.017 | 0.385 | 0.012 |
| RBP4 | --- | ↓ | 1.226 | 0.024 | 0.162 | 0.005 |
| Serpin E1 | --- | --- | 0.921 | 0.006 | 1.179 | 0.028 |
| Thrombospondin-1 | --- | ↓ | 0.774 | 0.011 | 0.401 | 0.009 |
| Vitamin D | --- | ↓ | 0.934 | 0.029 | 0.172 | 0.027 |

FIGURE 5

PREPARATION OF PLATELET PELLET LYSATE AND ITS USE FOR TREATING NEUROLOGICAL DISORDERS

This application is a National Stage Application of PCT/EP2017/057004 filed Mar. 23, 2017, which claims priority from European Patent Application No. 16305332.5 filed Mar. 23, 2016. Each of the prior mentioned applications is hereby incorporated by reference herein in its entirety.

The present invention relates to a process for obtaining a novel platelet pellet lysate, the platelet pellet itself and its use for treating neurological disorders such as neurodegenerative, neuroinflammatory, neurodevelopmental and/or neurovascular disorders (i.e. stroke), but also the consequences of cerebral insults (traumatic brain injury, hypoxia . . . ).

Developing effective "disease modifying strategy" providing neuroprotection, neurorestoration and neurogenesis to treat neurodegenerative disorders, such as Parkinson's disease (PD), amyotrophic lateral sclerosis (ALS), and Alzheimer disease (AD), is urgently needed considering the huge societal and economic impacts these disorders impose to patients and care-givers.

Developing effective treatments providing neurorestoration and neurogenesis in order to compensate for the loss of neurons and following insults of the central nervous system, such as severe hypoxia following delivery or cardiac arrest or severe traumatic brain injury, is also largely waited considering the lack of validated treatments.

There is substantial evidence that neurotrophins, as activators and modulators of neuronal signaling pathways, represent a logical therapeutic strategy for neurological disorders.[1] Application of single recombinant neurotrophic growth factors has provided encouraging results for neuronal protection and repair in both cell and animal models.[2,3]

Platelet-derived growth factor-CC (PDGF-CC) proved to be a potent neuroprotective factor in several animal models of neuronal injury[4] whereas PDGF-BB and brain-derived neurotrophic factor (BDNF), administered via intra cerebroventricular (ICV) route, stimulated neurogenesis.[5] In addition, systemic administration of BDNF in a photothrombotic model of focal stroke could induce neurogenesis and improve sensorimotor function.[6] Transforming growth factor-β (TGF-β) could promote the development and survival of dopaminergic neurons, and neuroprotection in animal models of parkinsonism,[7] and enhanced the trophic effect of glial-derived neurotrophic factor (GDNF) in hemiparkinsonian rats.[8]

Pre-clinical studies showed neuroprotection by basic-fibroblast growth factor (b-FGF)[9] and vascular endothelial growth factor-β (VEGF-β),[10] and promotion of neuroprotection and neurorestoration by GDNF.[11-15]

Unfortunately, all randomized clinical studies involving ICV administration of high-dose, single growth factors have failed to yield any substantial positive clinical effects.[16-18]

Currently, administering single neurotrophins in such complex and multifaceted neurodegenerative pathologies is insufficient to yield meaningful therapeutic outcomes.

Thus, there is a need to develop a novel approach combining several recombinant neurotrophins which would likely be more powerful, but this is conceptually challenging, thereby justifying more pragmatic strategies inspired from other fields of regenerative medicine.

Platelet concentrates are a well-established therapeutic product, on the WHO model list of essential medicines,[19] typically used in the prophylaxis and treatment of bleeding disorders resulting from thrombocytopenia.[20] Besides their role in haemostasis,[20,21] platelets exert crucial physiological functions in wound healing and tissue repair.[21-23]

The range of regenerative medicine[24] and cell therapy[25] applications where platelets and platelet lysates are evaluated is expanding. The therapeutic benefit of platelets in tissue healing is multifactorial and results from the myriad of bioactive mediators stored primarily in the a-granules and acting in synergy.[22-24,26] These include neurotrophic growth factors, such as PDGF (-AA, -AB and -BB isoforms), BDNF, VEGF, TGF-β, bFGF, or epithelium growth factor (EGF). Intracranial delivery of platelet lysates in animal models of stroke was recently shown to stimulate the proliferation of endogenous neural stem cells (eNSC) and angiogenesis in the subventricular zone and in the peri-lesion cortex, leading to improved functional outcomes and reduced injury, and suggesting neuroprotective effects.[27]

However, platelet lysates contain plasma-borne fibrinogen, a protein that plays a causative role in neurologic disorders as a potent inducer of inflammation and an inhibitor of neurite outgrowth.[35] This may be a reason why application of platelet lysates in the field of neurodegenerative disorders in humans, such as Parkinson's Disease, has not been reported yet.

The invention is based on the unexpected findings that, when platelet pellet lysate (PPL) is prepared under specific conditions, it is able to potentiate the treatment of neurological disorders by inducing better neuroprotective effect as well as neurorestoration.

Particularly, the inventors have discovered that heat-treatment during preparation of PPL reduces the total protein content of the lysate and promotes enhanced neuroprotective and neurorestoration potential.

Thus, in a first aspect, the present invention relates to a process for preparing a modified heat-treated platelet pellet lysate, said process comprising the steps of:
  a) Providing a platelet pellet lysate,
  b) Heat-treating the platelet pellet lysate at a temperature of 55° C. to 65° C. during 20 to 40 minutes,
  c) Purifying the heat-treated platelet pellet lysate of step b) so as to obtain a modified heat-treated platelet pellet lysate having a total protein content of less than 70% of the total protein content of the platelet pellet lysate of step a).

Surprisingly and unexpectedly, the so-obtained modified heat-treated PPL provides improved neuroprotection compared to non heat-treated PPL or PPL treated at 37° C. In vitro assays have shown that especially at low and high doses, viability of neuronal cells is significantly improved with modified heat-treated PPL. Moreover, modified heat-treated PPL induces neurorestoration in in vitro assays.

Without wanting to be bound by any theory the inventors believe that the neurorestoration and improved neuroprotective activity of the PPL of the invention are a result of its reduced total protein content. It is believed that the heat-treatment at a temperature of 55° C. to 65° C. induces precipitation of proteins leading, after step c) in which it is believed that the precipitated proteins are removed, to a total protein content in the modified heat-treated PPL according to the invention significantly lower than in the starting PPL. The modified heat-treated PPL has indeed a total protein content of less than 70% of the total protein content of the PPL of step a). Preferably, the total protein content is less than 60%, especially less than 50% of the total protein content of the PPL of step a). The total protein content of the modified heat-treated PPL may for example be 4-6 mg/mL.

The heat-treatment according to the invention may also lead to a different relative protein composition. For example, heat-treatment appears to remove plasma-borne fibrinogen not removed during the preparation of the starting PPL, as well as platelet fibrinogen, leading to a modified heat-treated PPL having reduced fibrinogen content.

Advantageously, the modified heat-treated PPL has less than 1.5 mg/mL, preferably less than 1 mg/mL, more preferably less than 0.5 mg/mL and even more preferably from 0.1 mg/mL to 0.3 mg/mL of fibrinogen. Moreover, the growth factor content of the PPL may also be altered by the heat-treatment according to the invention. It may for example lead to a significant relative decrease in BDNF, bFGF, EGF, and HGF concentrations, whereas VEGF and TGFβ concentrations remain substantially unchanged, compared to normal fresh PPL ($PPL^F$) or expired PPL ($PPL^E$). The term fresh PPL refers to platelet pellet lysate prepared from platelet concentrates processed within 5 days of collection (non-expired). The term expired PPL refers to platelet pellet lysate prepared from platelet concentrates processed over 5 days of storage.

In one embodiment, the relative content in growth factors of the modified platelet pellet lysate obtained from both $PPL^F$ and $PPL^E$, expressed per mg of total proteins, decreases significantly for BDNF, bFGF and HGF, remained unchanged for PDGF-AB and EGF, and increases significantly for TGFβ. The VEGF and PF4 contents remain unchanged for modified platelet pellet lysate obtained from $PPL^F$ and increases for modified platelet pellet lysate obtained from $PPL^E$.

In one embodiment, the modified heat-treated PPL has a PF4 content of more than 50%, preferably more than 60%, more preferably more than 70% of the PF4 content of the PPL of step a) of the process of the invention.

Heat-treatment step b) may preferably be performed at a temperature of 55° C. to 60° C., more preferably at a temperature of about 56° C. The most promising results in terms of reproducibility of neuroprotection and neurorestoration were indeed obtained for PPL treated at about 56° C.

In a preferred embodiment, the duration of the heat-treatment is about 30 minutes.

Moreover, after heat-treatment, the PPL may be cooled down for at least 5 minutes, preferably to a temperature of about 2 to 5° C., before purifying step c).

The purification of the heat-treated PPL may be carried out by any method known in the art, such as for example centrifugation or filtration.

Centrifugation may advantageously be carried out at a temperature of about 2 to 6° C., for example for at least 15 min at 9000×g to 11000×g.

When filtration is used, the heat-treated PPL is advantageously passed through a filter having a pore size from 5 μm to 0.2 μm, preferably a sequence of two or more successive filters having decreasing pore sizes with a respective pore size from 5 μm to 0.2 μm is used.

Advantageously, purification of the heat-treated PPL lysate in step c) is carried out by centrifugation. Without wanting to be bound by any theory, the inventors believe that centrifugation at low temperatures as described above may contribute to further removing cold-insoluble components, such as fibrinogen, which precipitate.

The process of the present invention may further comprise, after the heat-treatment step, a step of freezing and storing the modified heat-treated PPL obtained in step c) at a temperature range from −20° C. to −85° C., preferably from −25° C. to −50° C. and more preferably around −30° C. Alternatively, the modified heat-treated PPL may be freeze-dried before storing.

In a further embodiment, the process of the present invention further comprises after step c) and before optional freezing or freeze-drying, a step of viral inactivation such as solvent detergent treatment (S/D treatment) or pasteurization (heat-treatment at 60° C. for 10 hours in the presence of stabilizers) and/or a step of viral or prion removal by nanofiltration using dedicated virus filters of 15, 20, or 35 nm, or equivalent pathogen removal filters. Thus, the obtained modified heat-treated PPL is viral and prion safe. The term "viral inactivation" refers to a situation wherein viruses are maintained in the platelet pellet lysate but are rendered non-viable e.g. by dissolving their lipid coat or by destroying their virion structure.

The term "viral removal" refers to a situation wherein viruses, which have rigid large size structures, are removed from the platelet pellet lysate by retention on a filter while platelet pellet lysate components go through such virus removal filter and is recovered for further processing.[36,37].

The starting platelet pellet lysate (PPL) provided in step a) may be prepared according to well-known methods[38]. It may for example be prepared as follows:
 i. Providing a platelet concentrate
 ii. Centrifuging said platelet concentrate so as to obtain a platelet pellet and a first supernatant,
 iii. Removing the supernatant and suspending the pellet in a physiological buffer,
 iv. Freeze-thawing said suspended pellet,
 v. Centrifuging the suspension obtained in step iv) so as to obtain a platelet pellet lysate and second supernatant.

The platelet concentrate provided in step i) may be obtained by suitable standard collection methods from autologous or allogeneic platelet sources, in particular from whole blood, or by apheresis procedures, and suspended in plasma, or a combination of plasma and platelet additive solution, or platelet additive solution only[39]. Moreover, the platelet concentrate may be leukoreduced.

Suitable physiological buffers used in step iii) are for example phosphate buffer saline (PBS), HEPES buffer, Tris-HCl buffer or sodium acetate buffer, or physiological saline.

The platelet pellet lysate (PPL) used in step a) of the process according to the invention may be fresh PPL ($PPL^F$) or expired PPL ($PPL^E$), preferably $PPL^F$.

In a second aspect, the invention relates to a modified heat-treated PPL having a total protein content of less than 70%, less than 60%, more preferably less than 50% of the total protein content of non-heat-treated PPL. The total protein content of the modified heat-treated PPL may for example be 4-6 mg/mL. The modified heat-treated PPL according to the invention may be obtained by the process described hereabove. Advantageously, the modified heat-treated PPL of the invention has less than 1.5 mg/mL, preferably less than 1 mg/mL, more preferably less than 0.5 mg/mL and even more preferably from 0.1 mg/mL to 0.3 mg/mL of fibrinogen.

In one embodiment, the modified heat-treated PPL of the invention has a PF4 content of more than 50%, preferably more than 60%, more preferably more than 70% of the PF4 content of non-heat-treated PPL.

As set forth above, the modified heat-treated PPL of the invention provides neurorestoration and improved neuroprotective activity.

Thus, in a third aspect, the invention relates to the modified platelet pellet lysate according to the invention for use as a biological drug or "biotherapy", especially in the treatment and/or prevention of a neurological disorder and preferably a neurodegenerative disorder. In other terms, the invention also relates to a method of treating and/or preventing neurological disorders, comprising the administration of a therapeutically effective amount of the modified platelet pellet lysate of the invention, to a patient in need thereof. Preferably the patient is a warm-blooded animal, more preferably a human.

Neurological disorders within the meaning of present invention include but are not limited to neurodegenerative disorders; neurovascular disorders; neuroinflammatory disorders; neurodevelopmental disorders such as autism; cerebral insult such as severe hypoxia following delivery or cardiac arrest or severe cranial traumatism/traumatic brain injury that is to say severe insults resulting in a significant loss of neurons leading to handicap.

Neurodegenerative disorders within the meaning of the present invention include, but are not limited to multiple sclerosis (MS), Parkinson's disease (PD), Huntington's disease (HD), Amyotrophic lateral sclerosis (ALS), stroke, age-related macular degeneration (AMD), degenerative diseases of the retina, and dementia, the latter including, without being limited thereto, Alzheimer's disease (AD), vascular dementia, frontotemporal dementia, semantic dementia and dementia with Lewy bodies. Preferred neurodegenerative diseases are multiple sclerosis, Alzheimer's disease, Parkinson's disease, Huntington's disease, amyotrophic lateral sclerosis.

In a preferred embodiment, the neurodegenerative disorder is selected from Parkinson's disease, amyotrophic lateral sclerosis and Alzheimer's disease. In a particularly preferred embodiment, the neurodegenerative disorder is Parkinson's disease. In another preferred embodiment, the neurodegenerative disorder is amyotrophic lateral sclerosis.

Preferred other neurological disorders include insults of the central nervous system such as severe hypoxia following delivery or cardiac arrest or severe cranial traumatism that is to say severe insults resulting in a significant loss of neurons leading to handicap. The early treatment, with the modified heat-treated PPL, following the insult could enhance the physiological neurorestoration and neurogenesis abilities.

The modified heat-treated PPL may be administered as such, be encapsulated in natural or synthetic nanoparticles[40] or microparticles or be comprised in a pharmaceutical solution further comprising at least one pharmaceutically acceptable carrier, diluent, excipient and/or adjuvant. The pharmaceutical solution can further comprise complexes, molecules, peptides, salts, vectors or any other compound, which can ameliorate or can be beneficial in treatment neurological disorders.

The route of administration, and the dosage regimen naturally depend upon the severity of the illness, the age, weight, and sex of the patient, etc.

The modified heat-treated PPL of the invention may be used for the treatment of any patient, especially a warm-blooded animal such as a mammal and preferably a human.

Advantageously and as demonstrated by in vivo tests, the modified heat-treated PPL according to the invention is suitable for brain administration. Specifically, said modified heat-treated PPL is adapted for intra thecal (e.g. for amyotrophic lateral sclerosis which is a pathology of the spinal cord) or intra cerebroventricular (ICV) administration, for example into the right lateral ventricle, preferably closed to the intraventricular foramen so that the modified platelet pellet lysate can be administrated into the third ventricle. For example, a pump such as an ALZET® pump (commercialized by Alzet) can be used for this purpose.

The administration of the modified heat-treated PPL of the invention may also be performed by any other method known by the person skilled in the art, such as for example, intranasal, intramuscular or intraocular administration, or perfusion or infusion of an organ (i.e. direct infusion of a part of the brain tissue).

The exposure dosage used for the administration may be adapted as a function of various parameters, and in particular as a function of the mode of administration used, of the relevant pathology or of the desired duration of treatment.

Definitions

The definitions and explanations below are for the terms as used throughout the entire application, including both the specification and the claims.

By "neuroprotective activity" or "neuroprotection" is meant preservation of neuronal structure and/or function of neuronal cells affected by neurotoxin compared to neuronal cells which are not affected by neurotoxin. Neuroprotection aims to prevent or slow disease progression and secondary injuries by halting or at least slowing the loss of neurons. For example, it refers to preservation of the number of neurons in the striatum and/or in the substantia nigra pars compacta of patients affected by Parkinson's disease compared to patients who are not affected by Parkinson's disease.

By "neurorestoration" is meant compensation of existing alterations and stimulation of structural and functional restoring of the injured nervous activity.

The term "patient" refers to a warm-blooded animal, more preferably a human, who/which is awaiting or receiving medical care or is or will be the object of a medical procedure.

The term "human" refers to subjects of both genders and at any stage of development (i.e. neonate, infant, juvenile, adolescent, adult). In one embodiment, the human is an adolescent or adult, preferably an adult.

The terms "treat", "treating" and "treatment", as used herein, are meant to include alleviating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of modified platelet pellet lysate of the invention which is sufficient to achieve the desired therapeutic or prophylactic effect in the individual to which it is administered.

The term "administration", or a variant thereof (e.g., "administering"), means providing the modified platelet pellet lysate of the invention, alone or as part of a pharmaceutically acceptable solution, to the patient in whom/which the condition, symptom, or disorder is to be treated or prevented.

The present invention will be better understood with reference to the following examples and figures. These examples are intended to representative of specific embodiments of the invention, and are not intended as limiting the scope of the invention.

FIGURES

FIG. 1: Mode of preparation of Platelet lysate and Platelet Pellet Lysate from apheresis Platelet Concentrate.

Platelet lysate (PL) was obtained by 3 freeze/thaw cycles of platelet concentrate (PC). For platelet pellet lysate (PPL) preparation, platelets were pelleted to remove plasma, subjected to 3 freeze/thaw cycles, and centrifuged to remove the cell debris. Aliquots were frozen at −80° C. until tests.

Figure 2:
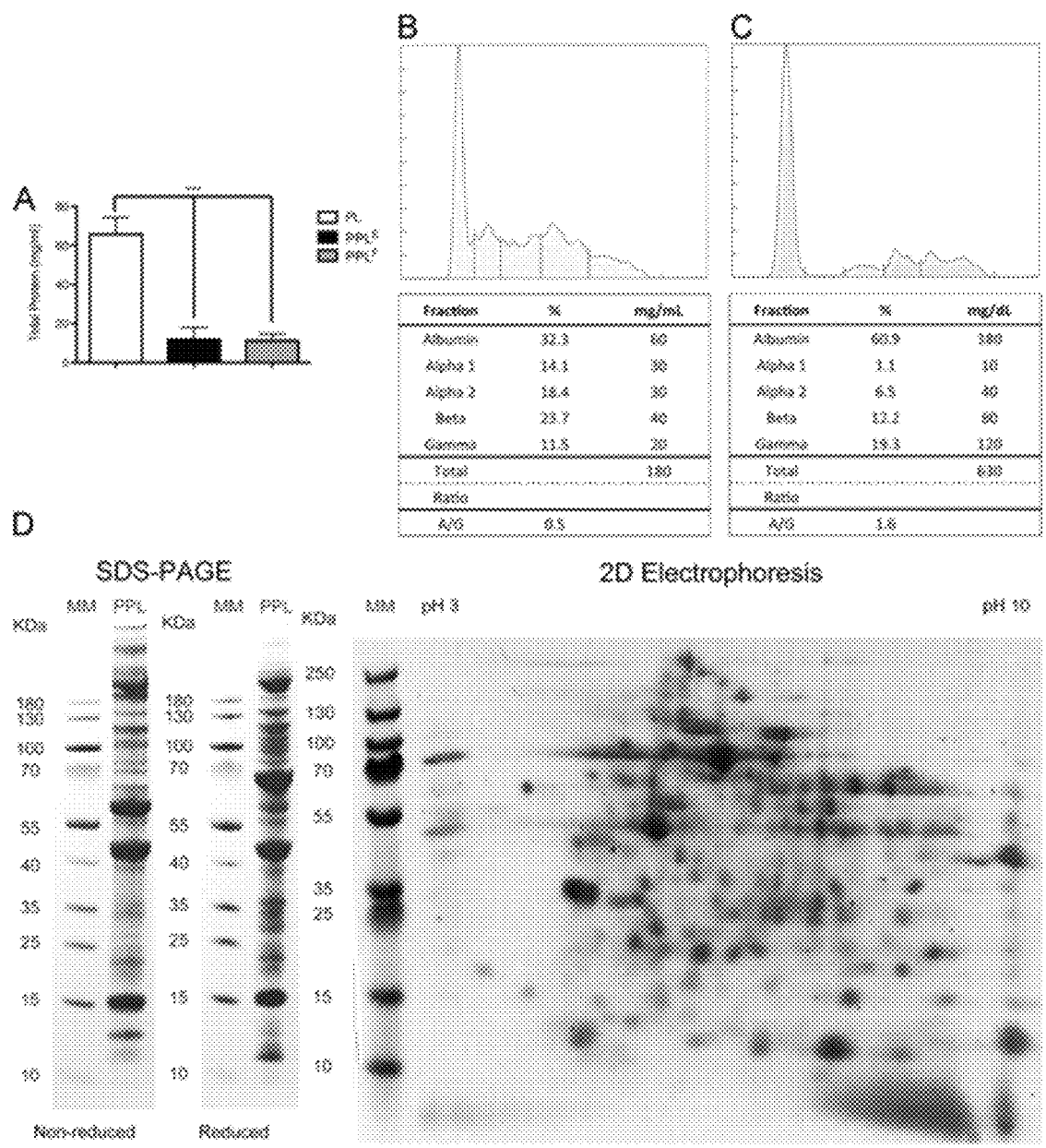

FIG. 2: Protein characterization of PL and PPL.

A: Comparative total protein content (mg/ml) of PL, $PPL^F$ and $PPL^E$.

B, C: Zone electrophoresis patterns of PL and PPL, respectively.

D: SDS-PAGE pattern of non-reduced and reduced PPL.

E: Two-dimensional electrophoresis pattern of PPL; isolectrofocusing separation was done at pH 3 to 10.

Figure 3:
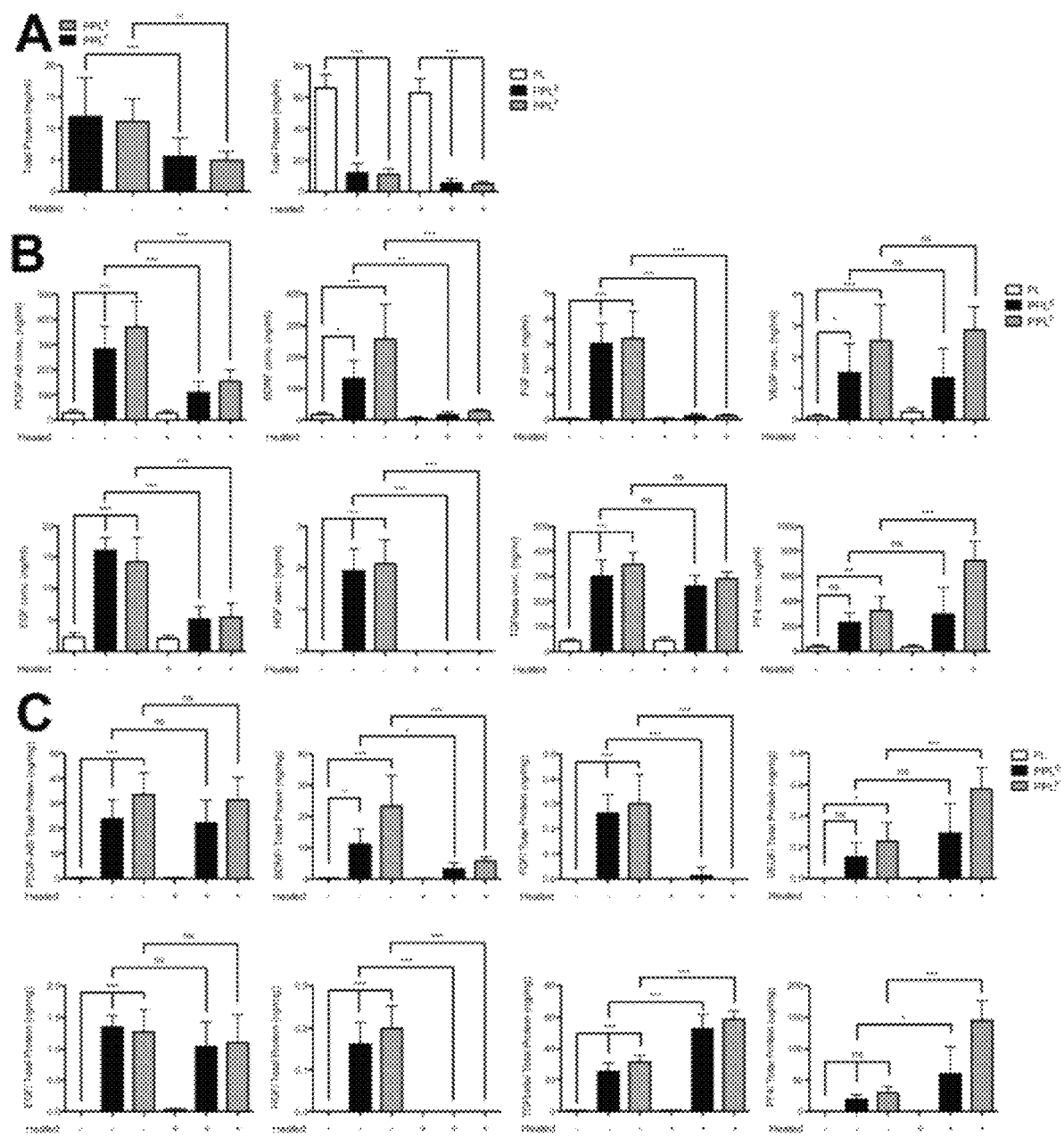

FIG. 3: Protein characterization of modified PPL heat-treated at 56° C. (+) (from $PPL^F$ and $PPL^E$) and PPL treated at 37° C. (−). A: Total protein content (mg/ml); Content expressed in ng/ml (B) and in ng/mg proteins (C) in PDGF-AB, BDNF, FGF, VEGF, EGF, HGF, THG-β, and PF4.

Figure 4:
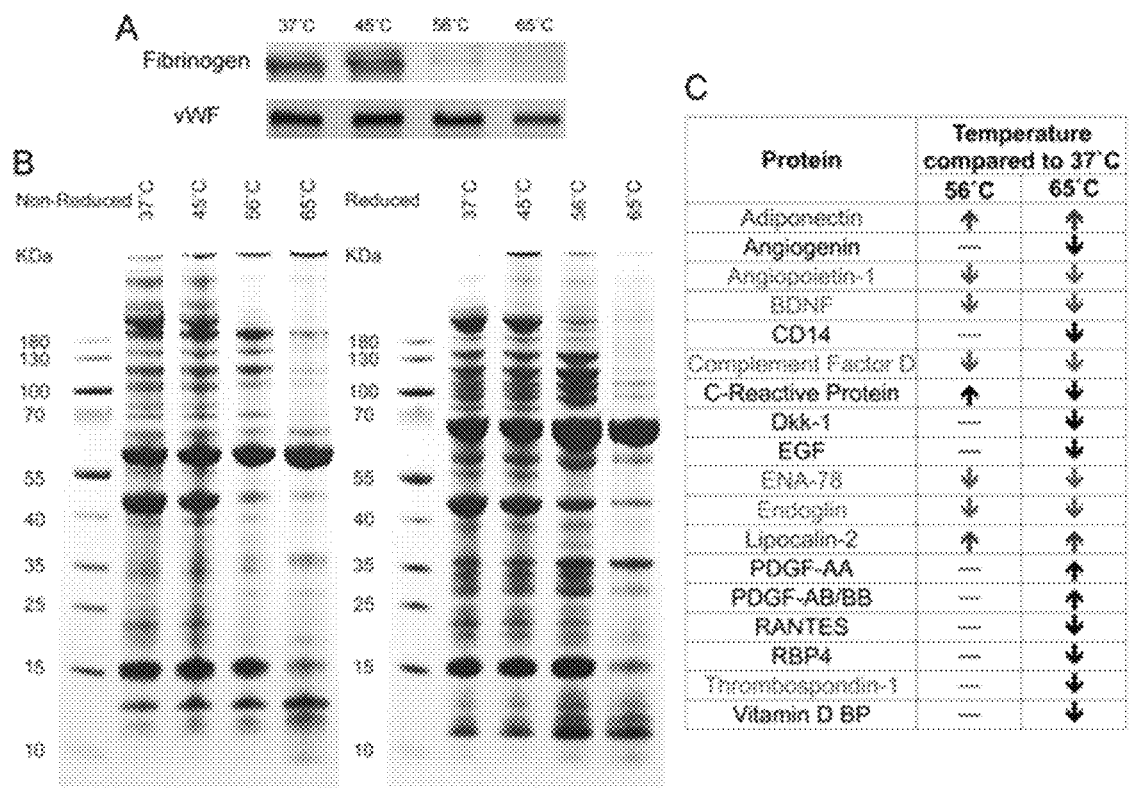

FIG. 4: Comparative protein composition of modified heat-treated PPL and PPL treated at 37° C. Western blot analysis of fibrinogen and vWF (A) and SDS-PAGE pattern under non-reducing and reducing conditions (B) of PPL treated at 37° C. (control PPL) or modified PPL heat-treated at 45, 56, or 65° C. C: Relative variations in cytokines in modified PPL heat-treated at 56° C. or 65° C. compared to PPL treated at 37° C. (control) as determined by cytokine array.

FIG. 5: Relative increase or decrease in various cytokines and proteins in modified PPL heat-treated at 56 or 65° C. compared to PPL treated at 37° C. (Control) determined by cytokine array. Data are expressed as average and standard deviation (SD).

Figure 6:
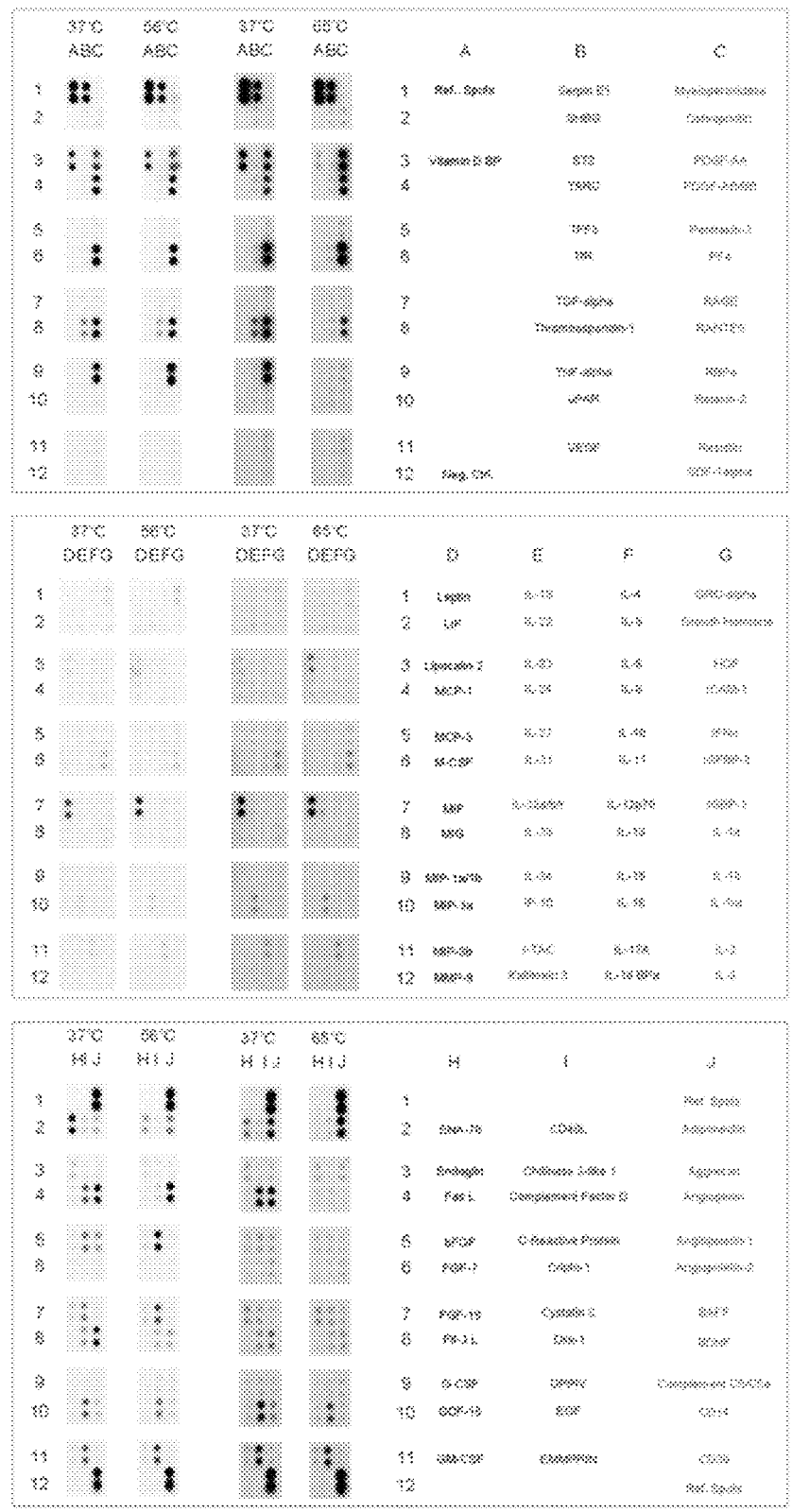

FIG. 6: Picture of cytokine arrays data in PPL treated at 37° C. (Control) or modified PPL heat-treated at 56 or 65° C.

Data are expressed as average and standard deviation (SD).

Figure 7:
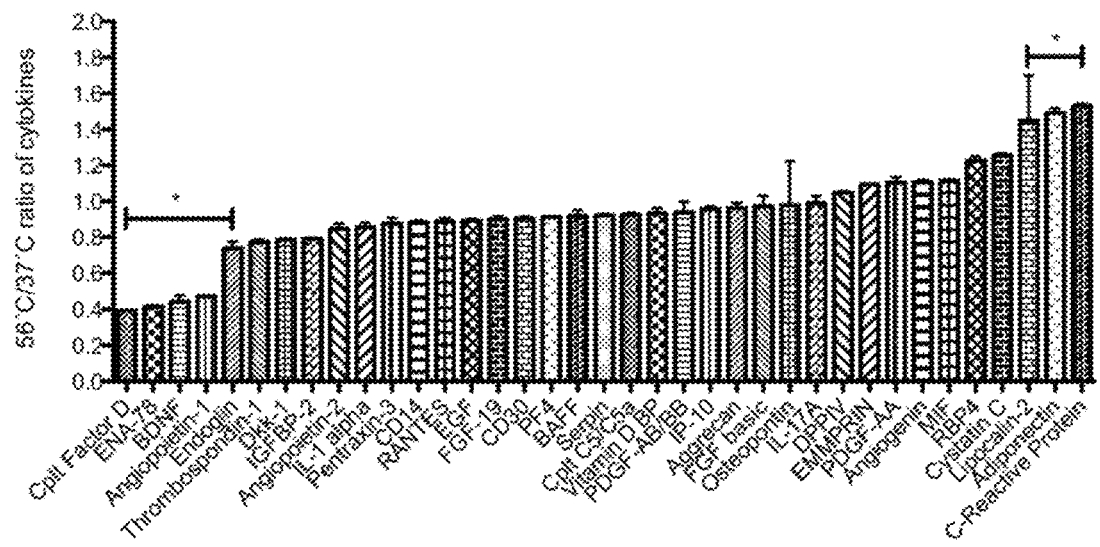

FIG. 7: Ratio of decrease and increase in cytokines in modified PPL heat-treated at 56° C. versus PPL treated at 37° C. (Control) detectable by cytokine array. *p<0.05.

Figure 8:
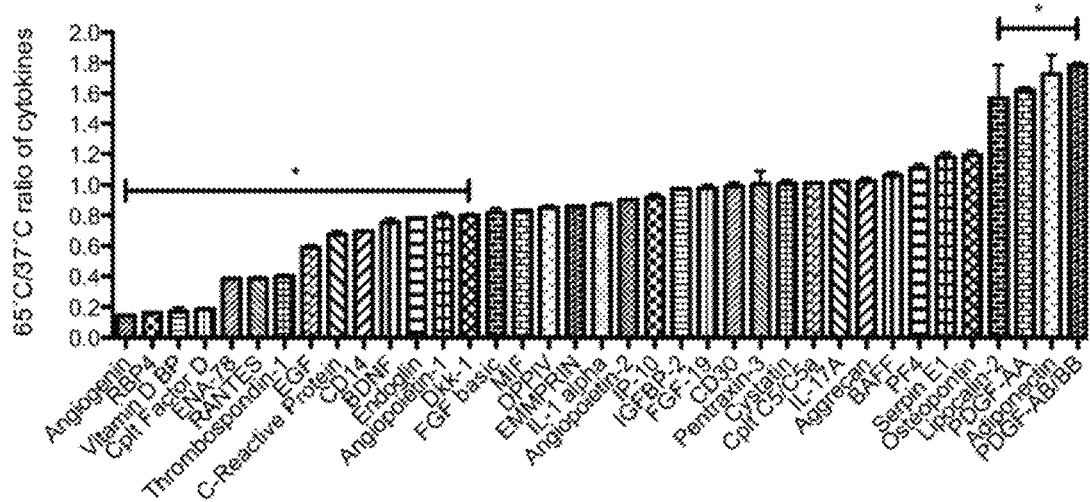

FIG. 8: Ratio of decrease and increase in cytokines in modified PPL heat-treated at 65° C. versus PPL treated at 37° C. (Control) detectable by cytokine array. *p<0.05.

Figure 9:
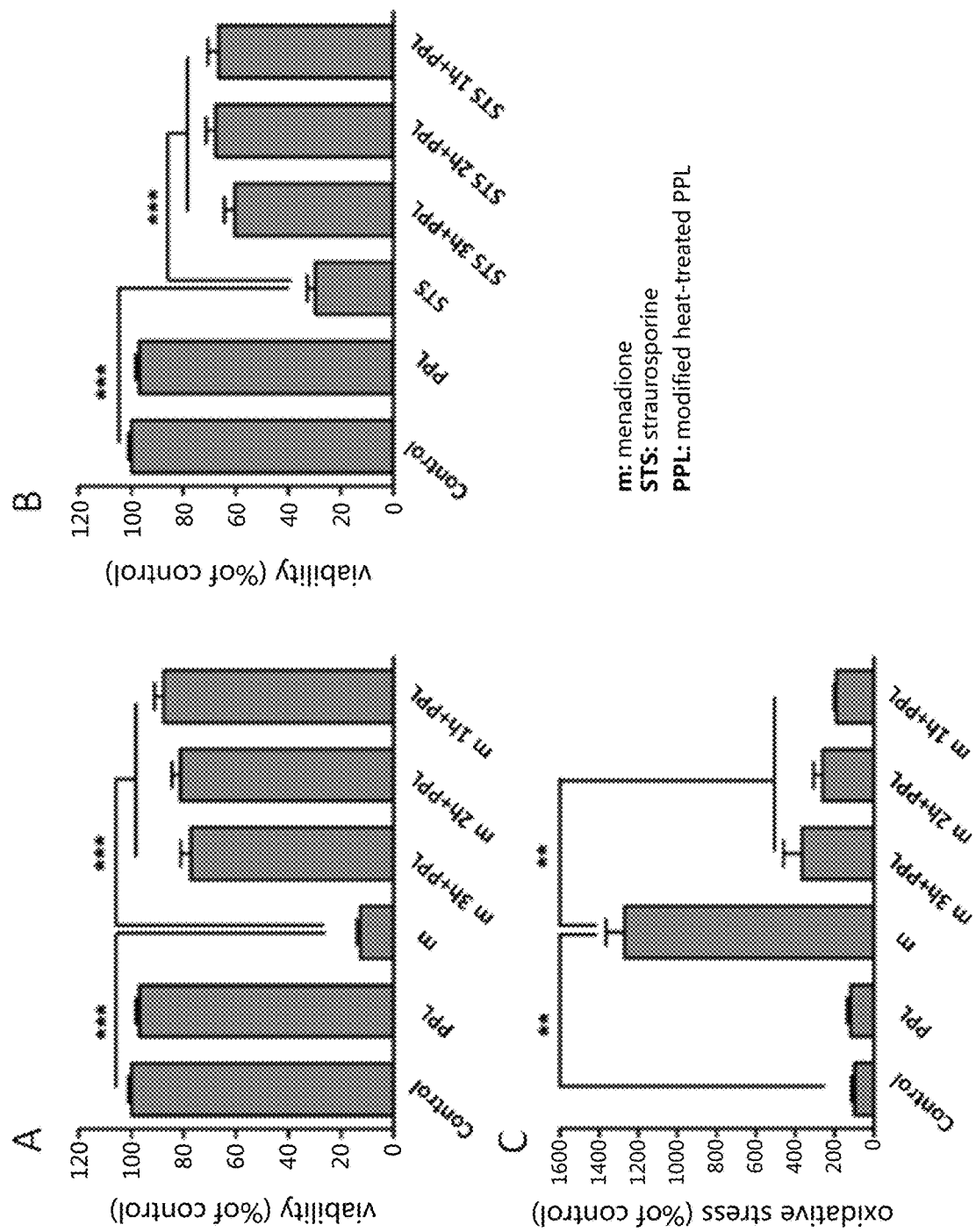

FIG. 9: Modified heat-treated PPL efficacy on neurorestoration

A: viability of NSC-34 cells treated with menadione prior to the addition of modified heat-treated PPL (56° C.).

Legend: PPL: modified heat-treated PPL, m: menadione, m3h+PPL: treatment with menadione 3h prior to the addition of modified heat-treated PPL, m2h+PPL: treatment with menadione 2h prior to the addition of modified heat-treated PPL, m1h+PPL: treatment with menadione 1h prior to the addition of modified heat-treated PPL.

B: viability of NSC-34 cells treated with straurosporine prior to the addition of modified heat-treated PPL (56° C.).

Legend: PPL: modified heat-treated PPL, STS: straurosporine, STS3h+PPL: treatment with straurosporine 3h prior to the addition of modified heat-treated PPL, STS2h+PPL: treatment with straurosporine 2h prior to the addition of modified heat-treated PPL, STS1h+PPL: treatment with straurosporine 1h prior to the addition of modified heat-treated PPL.

C: oxidative stress of NSC-34 cells treated with menadione prior to the addition of modified heat-treated PPL.

Figure 10:
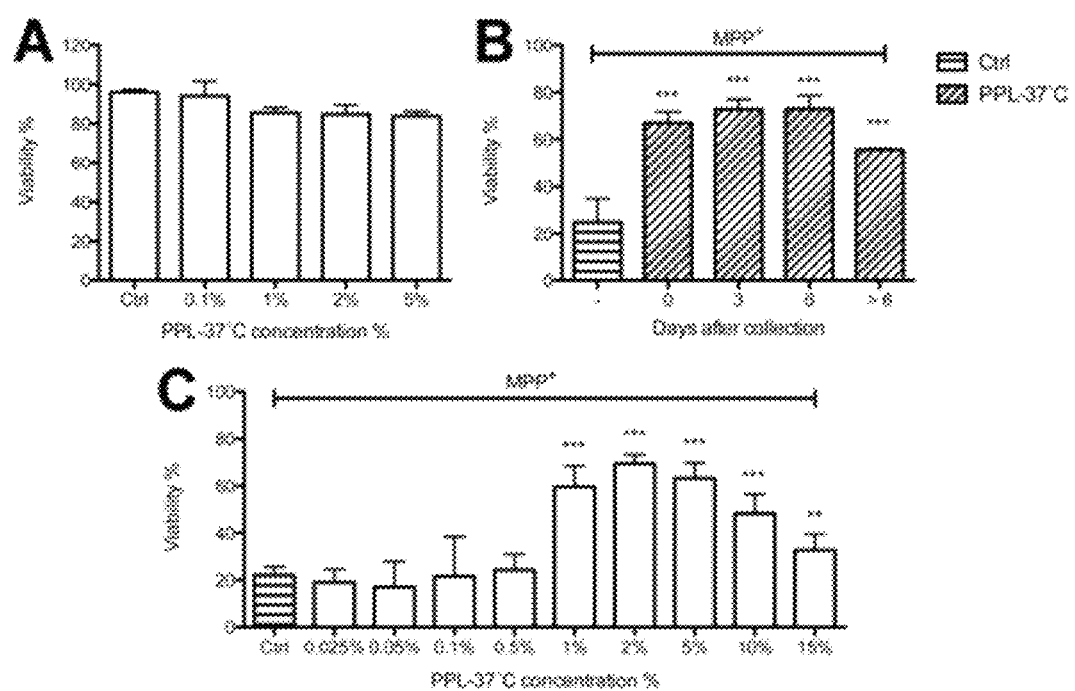

FIG. 10: Lack of toxicity and neuroprotective effect of the treatment of LUHMES by PPL.

A: Treatment by different concentration (0.1 to 5%) of PPL treated at 37° C. (PPL control) without MPP+-exposure.

B: Treatment by 2% PPL prepared from PC within one (0), 3, 6, and 7-10 days (>6) for one hour prior to exposure to 30 μM of MPP+.

C: Treatment by various doses (0.025-15%) of PPL treated at 37° C. (PPL control) prior to exposure to 30 μM of MPP+. Data are expressed as % of the viability of LUHMES cells grown in standard medium and not exposed to MPP+ (100%).

Figure 11:
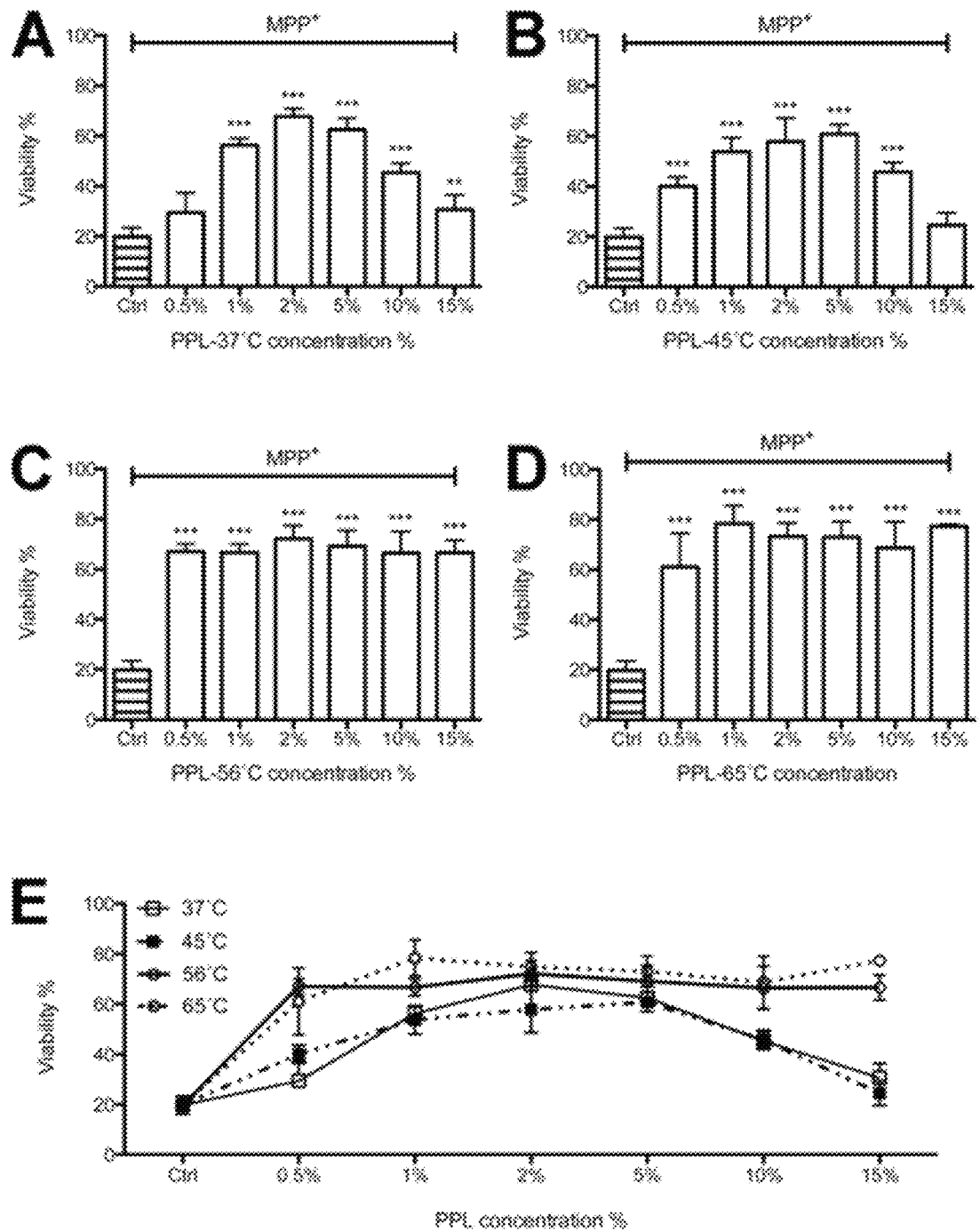

FIG. 11: Neuroprotective effect of the treatment of LUHMES cells by 0.5-15% of modified PPL heat-treated at 45° C., 56° C. and 65° C., or PPL treated at 37° C. prior to MPP+ exposure. PPL treated at 37° C. (A), or modified PPL heat-treated at 45° C. (B), 56° C. (C), or 65° C. (D). Extent of neuroprotection provided by treatment of LUHMES cells with increasing doses of PPL treated at 37° C. (Control) or modified PPL heat-treated at 45, 56, or 65° C. (E). Data are expressed as % of the viability of LUHMES cells grown in standard medium and not exposed to MPP+ (100%).

Figure 12:
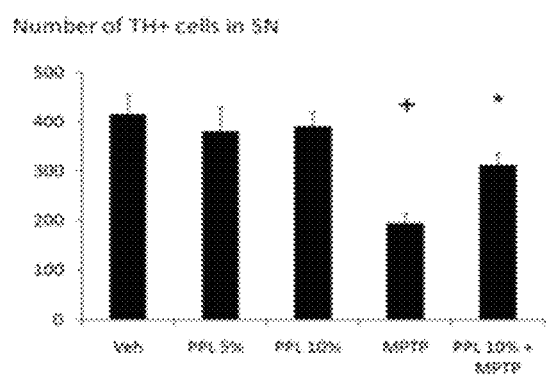

FIG. 12: Neuroprotective effects of PPLs in MPTP-intoxicated mice.

+: p<0.05 for the designated condition vs. the control condition; *:p<0.05 for the designated condition vs. the MPTP condition).

EXAMPLES

The following abbreviations are used throughout the entire description, figures and claims:
BAFF: B-cell-activating factor
BDNF: brain derived neurotrophic factor
C5/C5a: complement component 5/activated ;
CSF: cerebrospinal fluid
Ctrl: control
Dkk-1: Dickkopf WNT signaling pathway inhibitor 1
DPPIV: dipeptidyl peptidase IV
EGF: epithelium growth factor
EMMPRIN: extracellular matrix metalloproteinase inducer
ENA-78: epithelial-derived neutrophil-activating peptide78
FGF: fibroblast growth factor
FGF-β: fibroblast growth factor-β
Fas L: fas Ligand
G-CSF: granulocyte Colony stimulating factor
GDF-15: growth differentiation factor 15
HGF: hepatocyte growth factor
IGFBP-2: insulin-like Growth Factor Binding Protein-2
IL: interleukin
IP-10: interferon protein 10
I-TAC: interferon-inducible T-cell alpha chemoattractant
kDa: kilo Daltons
LIF: leukemia inhibitory factor
MCP: monocyte chemoattractant cytokine
MCP-1: monocyte chemoattractant cytokine 1
M-CSF: monocyte Colony stimulating factor
MIF: migration inhibition factor
MIG: monokine induced by Interferon gamma
MIP-1a/1b: macrophage inflammatory protein
MIP-3a: macrophage inflammatory protein
MM: molecular mass
MPP+: 1-methyl-4-phenylpyridinium
MMP: matrix metalloprotease
MMP-9: matrix metalloprotease 9
Neg Ctrl: negative control
PBS: phosphate buffer saline
PC: platelet concentrate
PDGF: platelet-derived growth factor PDGF-AB: platelet-derived growth factor-AB
PDGF-AB/BB: platelet-derived growth factor-AB/BB
PF4: platelet factor 4
PL: platelet lysate
PPL: platelet pellet lysate
$PPL^E$: platelet pellet lysate from expired PC
$PPL^F$: platelet pellet lysate from non-expired PC
RANTES: regulated on Activation Normal T cell Expressed and Secreted
RAGE: receptor for advanced glycation end products
RBP4: retinol-binding protein 4
SDS-PAGE: sodium-dodecyl-sulfate polyacrylamide gel electrophoresis
TGF-β: transforming growth factor-β
TNF: tumor necrosis factor.
SHBG: steroid Hormone Binding Globulin
ST2: interleukin 1 receptor-like 1
TARC: thymus and Activation Regulated Chemokine
TFF3: trefoil Factor Family 3
TfR: transferrin Receptor
uPAR: urokinase-Type Plasminogen Activator Receptor
VEGF: vascular endothelium growth factor
vWF: Von Willebrand Factor Materials and Methods Plasma and Platelet Collection The Institutional Review Board of Taipei Medical University approved the study (no. 201301020). Platelet concentrates were obtained from Taipei Blood Center (Guandu, Taiwan). They were collected from non-leukoreduced platelet concentrate obtained by apheresis (MCS®+; Haemonetics Corp., Braintree, Mass., USA) from volunteer healthy donors. Platelet and other blood cell count were determined on each donation, as previously described, using ABC Vet® (ABX Diagnostics, Montpellier, France).

Platelet concentrates were kept on a platelet agitator at 22±2° C.

Platelet concentrates processed within 5 days of collection (non- expired) were used to prepare $PPL^F$ ("fresh PPL"), while those with over 5 days of storage were used to prepare $PPL^E$ ("expired PPL").

Preparation of Platelet Pellet Lysate

The platelet lysates were prepared under aseptic conditions and as summarized in FIG. 1. A therapeutic-grade apheresis platelet concentrate suspended in plasma was used to prepare a platelet lysate (PL) control by three freeze-thaw cycles, at −80/30° C.±1° C., and centrifugation at 4500×g for 30 minutes at 22±2° C. to pellet and remove the cell debris. To prepare the platelet pellet lysates (PPL) used as starting material in step a) of the process of the invention, platelet concentrates (200-250 mL) were centrifuged (3000× g; 30 min; 22±2° C.), the plasma supernatant was carefully removed, and the surface of the pellet gently washed by 2 mL of sterile PBS. PBS (10% of the initial PC volume) was added, and the mixture pipetted gently to suspend the platelets that were then subjected to three freeze-thaw cycles (−80/+30±1° C.) and clarified by centrifugation (4500×g; 30 min; 22±2° C.). Aliquots (500 μl) of the PPL were kept frozen at −80° C. until use. Several heat-treated PPLs were prepared by heat-treatment in a dry bath at 45, 56, 65±1° C. for 30 min, and cooling down at least 5 minutes on ice then centrifuged (10000×g; 15 min; 4±2° C.). A control PPL was also prepared in the same manner using a dry bath at 37±1° C. The supernatant (heat-treated PPL or PPL treated at 37° C.) was then stored frozen at −80° C.

Protein Composition, Electrophoretic Profile and Western Blot Analysis of Platelet Pellet Lysate Total protein of the different PPLs was determined by micro-Bradford assay using bovine serum albumin as standard (Thermo Fischer Scientific, Waltham, Mass., USA) and NanoDrop™ (NanoDrop; Wilmington, Del., USA). Protein zone electrophoresis and lipoprotein electrophoresis were carried using SPIFE® 3000 (Helena, Tex., USA; 0.5 mL protein samples loaded). Sodium dodecyl sulfatepolyacrylamide gel electrophoresis (SDS-PAGE) was performed under non-reducing and reducing conditions using 4%-12% gradient gels, reagents, electrophoretic system from Invitrogen (Carlsbad, Calif., USA), and prestained protein molecular mass standard (Protein ladder, Thermo), as described before[30]. For two-dimensional gel electrophoresis, samples were first desalted using 2-D Clean-up kit (GE Healthcare, Little Chalfont, United Kingdom), isoelectrofocusing (Ettan IPGphor 3, GE Healthcare, Little Chalfont, United Kingdom), was performed at pH 3-10 gradient and SDS-PAGE using 4-12% polyacrylamide. Protein detection was done using Protein Gel Fast Stain Solution staining (Strong Biotech Corporation, Taipei, Taiwan).

Western blot analysis was conducted to detect fibrinogen and vWF. Briefly, heat treated PPL samples were mixed with 4× sample buffer (0.35 M Tris (pH 6.8), 10% w/v SDS, 30% v/v glycerol, 0.6 M DTT, and 0.012% w/v bromophenol blue) and heated to 95° C. for 5 min. Proteins were separated by SDS-PAGE, followed by transfer to polyvinylidene difluoride (PVDF) membranes. The membranes were blocked with 5% non-fat milk in TBS-0.1% Tween 20 and sequentially incubated with Rabbit anti-human fibrinogen antibody (GeneTex, California, USA) and Rabbit anti-human Von Willebrand Factor (vWF) antibody (Agilent's Dako, California, USA). HRP-conjugated secondary antibodies were used and followed by enhanced chemiluminescence (ECL) detection (GeneTex, California, USA).

Growth Factor and Cytokine Content by ELISA and Cytokine Array

Growth factors were determined in triplicates using Quantikine® ELISA kits (R&D Systems, Minneapolis, Minn., USA) following supplier's instructions, as previously described.[31-33]

Platelet pellet lysate samples were diluted 500-fold (for both 37° C. and 56° C.-treated samples) for PDGF-AB determination; 500- and 50-fold (37° C. and 56° C., respectively) for BDNF; 10-fold and without dilution (37° C. and 56° C., respectively) for bFGF; 5-fold (both 37° C. and 56° C.) for VEGF; 100-fold (both 37° C. and 56° C., respectively) for EGF; without dilution (both 37° C. and 56° C.) for HGF; 400-fold (both 37° C. and 56° C.) for TGF-β; and $1\times10^6$-fold for PF4.

Dilution factors were 200-fold, 100-fold, 1-fold, 2-fold, 50-fold, 2-fold, 100-fold, and $1\times10^5$-fold respectively for platelet lysate.

For TGF-β1 determination, 40 μL samples were acidified at 20 μL 1N HCl for 10 minutes then neutralized by 20 μL of 1.2 N NaOH/0.5 M HEPES.[31]

Human XL cytokine array was used to detect the relative content of 102 cytokines/growth factors in duplicates in 150 μg PPL, heat-treated or not at 56° C. or 65° C., following manufacturer's instructions (R&D Systems). Signal intensities were quantified using Imagine J software.

LUHMES Cells Maintenance and Differentiation

LUHMES cells were obtained from Dr. Scholz's laboratory (University of Konstanz, Germany) and cultured as described[28].

Briefly, undifferentiated LUHMES cells were propagated using Nunclon™ (Nunc, Roskilde, Denmark) plastic cell culture flasks and multi-well plates that were pre-coated with 50 µg/mL poly-L-ornithine and 1 µg/mL fibronectin (Sigma-Aldrich, St. Louis, MO, USA) in water for 3 h at 37° C. After removal of the coating solution, culture flasks were washed with sterile distilled water and air-dried. Cells were grown at 37° C. in a humidified 95% air, 5% $CO_2$ atmosphere. The proliferation medium was Advanced Dulbecco's modified Eagle's medium (Advanced DMEM)/F12 containing 1× N-2 supplement (Invitrogen, Karlsruhe, Germany), 2 mM L-glutamine (Gibco, Rockville, MD, USA) and 40 ng/mL recombinant bFGF (R&D Systems). When reaching approximately 80% confluence, cells were dissociated with a 0.025% trypsin solution (Gibco, Rockville, MD, USA) and passaged at $3\times10^6$ cells/flask. To induce differentiation intoneuronal cells, $2\times10^6$ LUHMES were seeded and grown into a T75 flask in proliferation medium for 24 h, then in Advanced DMEM/F12 containing 1× N-2 supplement, 2 mM L-glutamine (Gibco), 1 mM dibutyryl cAMP (Sigma-Aldrich), 1 µg/mL tetracycline (Sigma-Aldrich) and 2 ng/mL recombinant human GDNF (R&D Systems). After two days of culture in differentiation condition, LUHMES were cultured to 24-well plate for further experiments at day five.

LUHMES Cells Neurotoxic Stimulation and Viability Assay

Once differentiated (day 5), cells were exposed to various concentrations of Platelet Pellet Lysate (0.025 to 15%; v/v) for one hour followed by 30 µM MPP+ (Sigma-Aldrich). Cell viability was assessed after 48 h by MTT.

MTT (3-(4,5-dimethyl-2-thiazolyl)-2,5-diphenyl-2H-tetrazolium bromide) assay was added to the cell culture medium at 0.5 mg/ml (final concentration). After 1 h incubation at 37° C., the medium was removed and the purple crystals present in viable cells were lysed in DMSO under vigorous shaking for 10 min. An aliquot was transferred to a 96-well plate to detect the absorbance at 570 nm (690 nm as a background value).

Each condition was evaluated in duplicates using two different cell culture plates each containing controls. Data were expressed as % viability compared to controlled conditions where LUHMES were not exposed to MPP+.

Neurorestoration Induced by Modified Heat-Treated PPL (56° C.)

To prompt differentiation, neural stem cells (NSC-34) were grown in culture flasks in advanced DMEM/F12 supplemented with 0.5% FBS, 4 mM L-glutamine, 1% PS and 1 µM all trans retinoic acid for 2 days. Cells were then seeded in 24-well plates at a concentration of $3*10^4$ cell per well in differentiation medium with 0.5% FSB for 6 h. The medium was then replaced by FBS-free differentiation medium. After 3 days, medium was changed with retinoic-acid-free differentiation medium for treatment. NSC-34 cells were first treated with menadione or straurosporine (STS) for 1 h, 2 h or 3 h prior to the addition (5%) of modified heat-treated PPL for 24 h in total. Cell viability and oxidative stress were assessed by flow cytometry using propidium iodide and hydroethidine respectively. Statistical analysis was made by non parametric Mann Whitney test.

Stereotaxic Procedure and Platelet Pellet Lysate Infusion in a Mice 1-methyl-1,2,3,6-tetrahydropiridine Model (MPTP-Mice Model)

All animal procedures were conducted in compliance with national and international guidelines (Decree 87-848 of Oct. 19, 1987; French Ministry of Agriculture and Forestry, Veterinary Service for Animal Health and Welfare). The mice used were aged 5 months, with a 28 to 30 g body weight.

PPLs were injected at 1%, 2.5%, 5% and 10% of the estimated volume of cerebrospinal fluid (40 µL) in mice.

A brain cannula was inserted at the required anteroposterior and lateral stereotaxic coordinates (B 0.34 mm, L+1 mm, according to the Paxinos and Watson brain atlas) and then anchored to the skull with acrylic cement.

An ALZET® pump (Durect Corporation, Cupertino, Calif., USA) was filled with saline (control) or platelet pellet lysate, connected to a specific cannula and primed at 37° C. before surgery. The pump body was inserted subcutaneously on the mouse back just before insertion of the brain cannula. Two days after surgery, some of the mice were acutely intoxicated with MPTP (four intraperitoneal injections of 20 mg/kg of MPTP at 2 h intervals). The platelet pellet lysate was injected continuously over 7 days (5 days after intoxication) and mice were observed for sign of toxicity during the duration of the experiment.

Preliminary assessment of any neuroprotective effect of platelet pellet lysate was made by immunostaining and counting of tyrosine hydroxylase positive cells present in the substantia nigra. Mice anesthesia, formaldehyde perfusion, brain slice section, and incubation with antibodies and TH-positive neurons counting was done as described before[34].

Statistical Analysis

Results are expressed as the mean±standard deviation (SD). Statistical analyses were performed using one-way ANOVA after checking for the normal distribution of the data. Non-parametric texts of Wilcoxon and Kruskal-Wallis were performed in case of non-normal distribution. A P value of <0.05 was considered statistically significant.

Results

Blood Cell Count of Starting Platelet Concentrates and Characterization of Platelet Lysates The platelet concentrates used to prepare Platelet Pellet Lysate and Platelet Lysate had a mean count of $1240\pm252\times10^9$/L platelets, $0.08\pm0.05\times10^{12}$/L red blood cells, and $0.5\pm0.2\times10^9$/L white blood cells.

The protein composition of PPL was first characterized. The protein content (FIG. 2A) of $PPL^F$ and $PPL^E$ (approximately 11 mg/ml) was not significantly different (p>0.05), and much lower (p<0.001) than that of PL (ca. 65 mg/ml).

Zone electrophoresis patterns of PL (FIG. 2B) compared to $PPL^F$ (FIG. 2C) and/or $PPL^E$ (not shown) showed lower proportion of proteins migrating in the albumin and gamma region, and more as alpha 1, alpha 2, and beta, the albumin/gamma (A/G) being lower (0.5 vs 1.6).

SDS-PAGE pattern (FIG. 2D) of $PPL^F$ (and $PPL^E$; not shown) showed proteins with a wide distribution in molecular mass, with prominent bands at ca. 60, 48 and 15 kDa, and ca 68, 48, and 15 kDa under non-reducing and reducing conditions, respectively. 2D-electrophoresis pattern (FIG. 2D) showed that PPL is comprised of multiple components consistent with the complexity of the platelet proteome.

Thus, the characterization showed that Platelet Pellet Lysate has a unique protein composition compared to Platelet Lysate.

Heat-Treatment Modifies the Content in Proteins

Platelet Pellet Lysate was first treated at 56° C. for 30 min in order to obtain modified heat-treated PPL according to the invention.

Heat induced protein precipitation leading to a total protein content in the supernatant (FIG. 3A) significantly lower in both heat-treated $PPL^E$ (p<0.01) and $PPL^F$ (p<0.001) than in normal $PPL^F$, $PPL^E$ and PL control (p<0.001).

The content in growth factors, as measured by ELISA (FIG. 3B) or expressed per mg of proteins (FIG. 3C) was affected differentially by heat.

While concentration in PDGF-AB, BDNF, bFGF, EGF, and HGF decreased dramatically (p<0.001) compared to the respective non heat-treated $PPL^F$ or $PPL^E$, it remained no significantly different for VEGF, TGF-β and CXCL4/PF4 ($PPL^E$).

The relative content in growth factors in heat-treated $PPL^F$ and $PPL^E$ i.e. modified heat treated PPL, expressed per mg of total proteins, decreased significantly (p<0.001) for BDNF, bFGF, and HGF, remained unchanged (p>0.05) for PDGF-AB, VEGF (in $PPL^F$) and EGF and increased significantly (p<0.001) for VEGF (in $PPL^E$), TGF-β and PF4.

The impact of the heat-treatments at 45, 56, and 65° C. was explored on the SDS-PAGE profile of non-reduced or reduced PPL (FIG. 4B).

Heat-treatments at 56° C. and 65° C. led to major changes in protein composition characterized by removal of proteins of various molecular mass. Western blot analysis (FIG. 4A) indicated that heat treatments at 56° C. and 65° C. removed platelet-born fibrinogen (MM of approximately 270 kDa), whereas vWF remained relatively unaffected.

Arrays comparing cytokines in modified PPL heat-treated at 56° C. or 65° C. to PPL treated at 37° C. (Control) identified a relative enrichment in some PPL components (FIG. 4C, FIG. 5 and FIG. 6), including PDGF-AA, -AB/BB, and adiponectin, and a relative impoverishment in BDNF, EGF and others. Moreover, the cytokines ratio of modified PPL heat-treated at 56° C. or 65° C. versus PPL treated at 37° C. indicated a content relative variation.

Indeed, ratios of modified PPL heat-treated at 56° C. versus PPL treated at 37° C. indicate that relative contents of lipocalin-2, adinopectin, and C-reactive protein increased while relative contents of complement factor D, ENA-78, BDNF, angiopoietin-1 and endoglin are decreased (FIG. 7).

Ratios of modified PPL heat-treated at 65° C. versus PPL treated at 37° C. indicate increased relative contents of lipocalin-2, adinopectin, PDGF-AA and PDGF-AB/BB while relative contents of complement factor D, ENA-78, BDNF, angiopoietin-1, endoglin, Dkk-1, CD14, C-reactive protein, EGF, Thrombospondin-1, RANTES, RBP4, vitamin D and angiogenin are decreased (FIG. 8).

Platelet Pellet Lysates Protect LHUMES Cells Viability and Exert Significant Neuroprotective Activity when Added Prior to MPP+ and Heat Treatment Improves Platelet Pellet Lysate Neuroprotective Activity.

To further prove PPL neuroprotective capacity in vitro, the lack of toxicity of 0.1-5% (v/v) PPL to LUHMES cells (FIG. 10A) was first verified.

FIG. 10B illustrates that 1 hr-pre-treatment of the cells with 2% $PPL^F$ and $PPL^E$ exerted highly significant (p<0.001) protection against 30 μM of MPP+, as revealed by MTT assay.

When treated with various doses of $PPL^F$ (from 0.025 to 15%) a dose-response effect was observed with maximum neuroprotection achieved 2% $PPL^F$ treatment (FIG. 10C).

Therefore, both $PPL^F$ and $PPL^E$ protect LUHMES cells against MPP+ neurotoxin assault.

Regarding neuroprotective activity, 0.5-15% PPL, PPL treated at 37° C. (FIG. 11A), or modified PPL heat-treated at 45° C. (FIG. 11B), 56° C. (FIG. 11C), or 65° C. (FIG. 11D) maintained highly significant neuroprotective activity even at a concentration as low as 0.5%. The heat-treatment at 56° C. led to improved cell viability at lower doses. LUHMES cells treated with 0.5% dose of modified heat-treated PPL at 56° C. or 65° C. exhibit better viability than LUHMES cells treated with 0.5% of PPL treated at 37° C. (control). This qualitative improvement is also observed with 15% dose of heat-treated PPL at 56° C. and 65° C.

FIG. 11E comparing neuroprotection by various doses of PPLs shows that efficacy remains similar in the 0.5-15% range for the PPLs treated at the highest temperatures (56 and 65° C.).

By contrast, a dose-response effect is seen with non heat-treated PPL, or PPL heated only at 45° C. suggesting lack of efficacy at the lower dosages (0.5%), or toxicity or inhibitory effect at higher dosages (10-15%) likely due to protein overload.

Platelet Pellet Lysate Intra Cerebro Ventricular Infusion in Mice Did Not Induce Acute Toxicity and Provided Neuroprotection and Neurorestoration Experiments to validate the possibility for ICV injection of PPL treated at 37° C. and modified heat-treated PPL according to the invention showed that there was no apparent harmful effect at the four selected dosages (1%, 2.5%, 5% and 10%). There was no immediate detectable toxic effect following PPL infusion over the week duration of the experiment. The death rate associated with the procedure was low (1 out of 10 animals).

Cytometry analysis evidenced that NCS-34 cells viability is almost completely restored with a treatment by modified heat-treated PPL after 1 h, 2 h or 3 h exposure to neurotoxics menadione or straurosporine (FIG. 9A and 9B). These results show that modified heat-treated PPL according to the invention induces neurorestoration. Assessment of oxidative stress corroborates these results. Indeed, oxidative stress induced by menadione treatment (+1200% expressed in percentage of control) was reduced close to normal values by post treatment with modified heat-treated PPL according to the invention (FIG. 9C). Detection and counting of TH-positive neurons in the substantia nigra (FIG. 12) evidenced, as expected, the significant (p<0.05) neurotoxic effect of MPTP compared to the control vehicle solution (Veh). 5 or 10% PPL alone did not have significant effect on the number of TH-positive cells. Interestingly, we observed that 10% exhibited a strong and significant (p<0.05) neuroprotective effect against MPTP. Thus, ICV infusion of PPL appears to be safe at doses up to at least 10% of the total CFS volume, which provided neuroprotection against MPTP intoxication.

Treatment of NCS-34 cells after 1 h, 2 h or 3 h exposure to neurotoxics menadione or straurosporine was also carried out with PPL treated at 37° C. The results of this experiment show that although neuroprotection is obtained, it is 20% lower compared to a treatment with modified heat-treated PPL as described above (see FIGS. 9A and 9B).

REFERENCES

1. Huang E J, Reichardt L F. Neurotrophins: roles in neuronal development and function. Annu Rev Neurosci 2001;24: 677-736.
2. Aron L, Klein R. Repairing the parkinsonian brain with neurotrophic factors. Trends Neurosci 2011;34: 88-100.
3. Hefti F, Hartikka J, Knusel B. Function of neurotrophic factors in the adult and aging brain and their possible use in the treatment of neurodegenerative diseases. Neurobiol Aging 1989;10:515-33.
4. Tang Z S, Arjunan P, Lee C, et al. Survival effect of PDGF-CC rescues neurons from apoptosis in both brain and retina by regulating GSK3 beta phosphorylation. Journal of Experimental Medicine 2010;207: 867-80.
5. Mohapel P, Frielingsdorf H, Haggblad J, et al. Platelet-derived growth factor (PDGF-BB) and brain-derived neurotrophic factor (BDNF) induce striatal neurogenesis in adult rats with 6-hydroxydopamine lesions. Neuroscience 2005;132: 767-76.
6. Schabitz W R, Steigleder T, Cooper-Kuhn C M, et al. Intravenous brain-derived neurotrophic factor enhances poststroke sensorimotor recovery and stimulates neurogenesis. Stroke 2007;38:2165-72.
7. Roussa E, von Bohlen and Halbach O, Krieglstein K. TGF-beta in dopamine neuron development, maintenance and neuroprotection. Adv Exp Med Biol 2009; 651: 81-90.
8. Gonzalez-Aparicio R, Flores J A, Fernandez-Espejo E. Antiparkinsonian trophic action of glial cell line-derived neurotrophic factor and transforming growth factor beta 1 is enhanced after co-infusion in rats. Experimental Neurology 2010;226: 136-47.
9. Timmer M, Cesnulevicius K, Winkler C, et al. Fibroblast growth factor (FGF)-2 and FGF receptor 3 are required for the development of the substantia nigra, and FGF-2 plays a crucial role for the rescue of dopaminergic neurons after 6-hydroxydopamine lesion. J Neurosci 2007;27: 459-71.
10. Falk T, Yue X, Zhang S, et al. Vascular endothelial growth factor-B is neuroprotective in an in vivo rat model of Parkinson's disease. Neurosci Lett 2011;496: 43-7.
11. Hoffer B J, Hoffman A, Bowenkamp K, et al. Glial cell line-derived neurotrophic factor reverses toxin-induced injury to midbrain dopaminergic neurons in vivo. Neurosci Lett 1994;182: 107-11.
12. Kearns C M, Gash D M. GDNF protects nigral dopamine neurons against 6-hydroxydopamine in vivo. Brain Res 1995;672: 104-11.
13. Tomac A, Lindqvist E, Lin L F, et al. Protection and repair of the nigrostriatal dopaminergic system by GDNF in vivo. Nature 1995;373: 335-9.
14. Gash D M, Zhang Z, Ovadia A, et al. Functional recovery in parkinsonian monkeys treated with GDNF. Nature 1996;380: 252-5.
15. Kirik D, Georgievska B, Bjorklund A. Localized striatal delivery of GDNF as a treatment for Parkinson disease. Nat Neurosci 2004;7: 105-10.
16. Ruozi B, Belletti D, Bondioli L, et al. Neurotrophic factors and neurodegenerative diseases: a delivery issue. Int. Rev. Neurobiol 2012;102: 207-47.
17. Nutt J G, Burchiel K J, Comella C L, et al. Randomized, double-blind trial of glial cell line-derived neurotrophic factor (GDNF) in PD. Neurology 2003;60: 69-73.
18. Rodrigues T M, Jeronimo-Santos A, Outeiro T F, et al. Challenges and Promises in the Development of Neurotrophic Factor-Based Therapies for Parkinson's Disease. Drugs & Aging 2014;31: 239-61.
19. Klein H G. Should blood be an essential medicine? N Engl J Med 2013;368: 199-201.
20. Golebiewska E M, Poole A W. Platelet secretion: From haemostasis to wound healing and beyond. Blood Rev 2015;29: 153-62.
21. Nurden A T, Nurden P, Sanchez M, et al. Platelets and wound healing. Front Biosci 2008;13: 3532-48.
22. Barrientos S, Stojadinovic O, Golinko M S, et al. Growth factors and cytokines in wound healing. Wound Repair Regen 2008;16: 585-601.
23. Golebiewska E M, Poole A W. Platelet secretion: From haemostasis to wound healing and beyond. Blood Rev 2014.
24. Burnouf T, Goubran H A, Chen T M, et al. Blood-derived biomaterials and, platelet growth factors in regenerative medicine. Blood Rev 2013;27: 77-89.
25. Burnouf T, Strunk D, Koh M, et al. Human platelet lysate: replacing fetal bovine serum as a gold standard for human cell propagation? Biomaterials 2016;76: 371-87.
26. Blair P, Flaumenhaft R. Platelet alpha-granules: basic biology and clinical correlates. Blood Rev 2009;23: 177-89.
27. Hayon Y, Dashevsky O, Shai E, et al. Platelet lysates stimulate angiogenesis, neurogenesis and neuroprotection after stroke. Thromb Haemost 2013;110: 323-30.
28. Scholz D, Poltl D, Genewsky A, et al. Rapid, complete and large-scale generation of post-mitotic neurons from the human LUHMES cell line. J Neurochem 2011;119: 957-71.
29. Burnouf T, Chou M L, Wu Y W, et al. Antimicrobial activity of platelet (PLT)-poor plasma, PLT-rich plasma, PLT gel, and solvent/detergent-treated PLT lysate biomaterials against wound bacteria. Transfusion 2013;53: 138-46.
30. Su C Y, Kuo Y P, Nieh H L, et al. Quantitative assessment of the kinetics of growth factors release from platelet gel. Transfusion 2008;48: 2414-20.
31. Burnouf T, Chang C W, Kuo Y P, et al. A chromatographically purified human TGF-betal fraction from virally inactivated platelet lysates. Vox Sang 2011;101: 215-20.
32. Burnouf T, Kuo Y P, Blum D, et al. Human platelet concentrates: a source of solvent/detergent-treated highly enriched brain-derived neurotrophic factor. Transfusion 2012;52: 1721-8.
33. Su C Y, Kuo Y P, Lin Y C, et al. A virally inactivated functional growth factor preparation from human platelet concentrates. Vox Sang 2009;97: 119-28.
34. Laloux C, Derambure P, Kreisler A, et al. MPTP-treated mice: long-lasting loss of nigral TH-ir neurons but not paradoxical sleep alterations. Experimental Brain Research 2008;186: 635-42.
35. J. K. Ryu, D. Davalos and K. Akassoglou. Fibrinogen signal transduction in the nervous system. Journal of thrombosis and heamostasis. 2009; Vol. 7, issue supplement s1, 151-154.
36. Burnouf T, Radosevich M. Nanofiltration of plasma bio-pharmaceutical products [invited review]. Haemophilia, 2003, 9: 24-37.
37. Burnouf T, Radosevich M, Goubran H A, Wilkommen, H. Place of nanofiltration for assuring viral safety of biologicals. Current Nanoscience, 2005; 1: 189-201
38. Yael Hayon; Olga Dashevsky; Ela Shai; David Varon; Ronen R. Leker Platelet lysates stimulate angiogenesis, neurogenesis and neuroprotection after stroke. Thromb Haemost 2013; 110: 323-330
39. Shih D T B, Burnouf T. Human blood platelet growth factors supplements for ex vivo stem cell expansion (invited review). New Biotechnology, 2015:32; 199-211.
40. Victor E. Santo, Manuela E.Gomes, Joao F. Mano and Rui L; Reis. Chitosan-chondroitin sulphate nanoparticles for controlled delivery of platelet lysates in bone regenerative medicine. Journal of Tissue Engineering and Regenerative Medicine. December 2012, vol.6, issue S3, pages s47-s59.

The invention claimed is:
1. A method for treating a neurological disorder selected from Parkinson's disease and amyotrophic lateral sclerosis, comprising a step of administering an effective amount of a platelet pellet lysate which is modified by a heat treatment at a temperature of 55° C. to 65° C. for 20 to 40 minutes to a patient in need thereof, said lysate having a total protein content of less than 70% of the total protein content of non-heated platelet pellet lysate, wherein the platelet pellet lysate is prepared using a method comprising steps of:
  i. providing a platelet concentrate from human blood;
  ii. centrifuging the platelet concentrate to obtain a platelet pellet and a plasma supernatant;
  iii. removing the plasma supernatant and suspending the platelet pellet;
  iv. subjecting the suspended platelet pellet to freeze/thaw cycles to lyse platelets of the suspended platelet pellet and obtain a suspension; and
  v. removing cell debris of the suspension obtained in step iv by centrifugation to obtain a platelet pellet lysate.

2. The method according to claim 1, wherein the platelet pellet lysate is administered by intrathecal, intraocular, intranasal or intra cerebroventricular route.

3. The method of claim 1, wherein said platelet pellet lysate is administered by intra cerebroventricular route.

4. The method of claim 1, wherein said platelet pellet lysate is administered with a pump.

5. The method of claim 1, wherein said platelet pellet lysate has a total protein content of less than 60% of the total protein content of non heat-treated platelet pellet lysate.

6. The method of claim 1, wherein said platelet pellet lysate has a total protein content of less than 50% of the total protein content of non heat-treated platelet pellet lysate.

7. The method of claim 1, wherein said platelet pellet lysate is administered into the right lateral ventricle.

8. The method of claim 1, wherein said platelet pellet lysate is administered into the third ventricle.

9. A method for treating Parkinson's disease, comprising a step of administering an effective amount of a platelet pellet lysate which is modified by a heat treatment at a temperature of 55°° C. to 65° C. for 20 to 40 minutes to a patient in need thereof, said lysate having a total protein content of less than 70% of the total protein content of non-heated platelet pellet lysate, wherein the platelet pellet lysate is prepared using a method comprising steps of:
  i. providing a platelet concentrate from human blood;
  ii. centrifuging the platelet concentrate to obtain a platelet pellet and a plasma supernatant;
  iii. removing the plasma supernatant and suspending the platelet pellet;
  iv. subjecting the suspended platelet pellet to freeze/thaw cycles to lyse platelets of the suspended platelet pellet and obtain a suspension; and
  v. removing cell debris of the suspension obtained in step iv by centrifugation to obtain a platelet pellet lysate.

10. The method according to claim 9, wherein the platelet pellet lysate is administered by intrathecal, intraocular, intranasal or intra cerebroventricular route.

11. The method of claim 9, wherein said platelet pellet lysate has a total protein content of less than 60% of the total protein content of non heat-treated platelet pellet lysate.

12. The method of claim 9, wherein said platelet pellet lysate has a total protein content of less than 50% of total protein content of non heat-treated platelet pellet lysate.

13. The method of claim 9, wherein said platelet pellet lysate is administered into the right lateral ventricle.

14. The method of claim 9, wherein said platelet pellet lysate is administered into the third ventricle.

15. A method for treating amyotrophic lateral sclerosis, comprising a step of administering an effective amount of a platelet pellet lysate which is modified by a heat treatment at a temperature of 55° C. to 65° C. for 20 to 40 minutes to a patient in need thereof, said lysate having a total protein content of less than 70% of the total protein content of non-heated platelet pellet lysate, wherein the platelet pellet lysate is prepared using a method comprising steps of:
  i. providing a platelet concentrate from human blood;
  ii. centrifuging the platelet concentrate to obtain a platelet pellet and a plasma supernatant;
  iii. removing the plasma supernatant and suspending the platelet pellet;
  iv. subjecting the suspended platelet pellet to freeze/thaw cycles to lyse platelets of the suspended platelet pellet and obtain a suspension; and
  v. removing cell debris of the suspension obtained in step iv by centrifugation to obtain a platelet pellet lysate.

16. The method according to claim 15, wherein the platelet pellet lysate is administered by intrathecal, intraocular, intranasal or intra cerebroventricular route.

17. The method of claim 15, wherein said platelet pellet lysate has a total protein content of less than 60% of the total protein content of non heat-treated platelet pellet lysate.

18. The method of claim 15, wherein said platelet pellet lysate has a total protein content of less than 50% of total protein content of non heat-treated platelet pellet lysate.

19. The method of claim 15, wherein said platelet pellet lysate is administered into the right lateral ventricle.

20. The method of claim 15, wherein said platelet pellet lysate is administered into the third ventricle.

21. The method according to claim 1, wherein the platelet pellet lysate is modified by the heat treatment for 30 minutes.

22. The method according to claim 1, wherein the platelet pellet lysate is modified by the heat treatment at 56° C.

23. The method according to claim 21, wherein the platelet pellet lysate is modified by the heat treatment at 56° C.

24. The method according to claim 1, wherein following the heat treatment the platelet pellet lysate is purified by centrifugation or filtration.

25. The method according to claim 23, wherein following the heat treatment, the platelet pellet lysate is purified by centrifugation or filtration.

* * * * *